(12) United States Patent
Han

(10) Patent No.: US 11,596,947 B2
(45) Date of Patent: Mar. 7, 2023

(54) ALL-IN-ONE SELF TEST KIT

(71) Applicant: Kyung-Joon Han, Chungcheongnam-do (KR)

(72) Inventor: Kyung-Joon Han, Chungcheongnam-do (KR)

( * ) Notice: Subject to any disclaimer, the term of this patent is extended or adjusted under 35 U.S.C. 154(b) by 0 days.

(21) Appl. No.: 17/591,947

(22) Filed: Feb. 3, 2022

(65) Prior Publication Data
US 2023/0036013 A1 Feb. 2, 2023

(30) Foreign Application Priority Data

Jul. 29, 2021 (KR) .................. 10-2021-0099715

(51) Int. Cl.
*B01L 3/00* (2006.01)
*G01N 1/14* (2006.01)
*G01N 33/543* (2006.01)

(52) U.S. Cl.
CPC ............. *B01L 3/5029* (2013.01); *G01N 1/14* (2013.01); *G01N 33/54391* (2021.08); *B01L 2200/0689* (2013.01); *B01L 2200/16* (2013.01); *B01L 2300/042* (2013.01); *B01L 2300/0825* (2013.01); *B01L 2300/0832* (2013.01)

(58) Field of Classification Search
CPC ........... B01L 3/5029; B01L 2200/0689; B01L 2200/16; B01L 2300/042; B01L 2300/0825; B01L 2300/0832; G01N 1/14; G01N 33/54391
See application file for complete search history.

(56) References Cited

U.S. PATENT DOCUMENTS

| 2007/0275475 | A1 | 11/2007 | Liang |
| 2017/0189900 | A1 | 7/2017 | Wan et al. |
| 2019/0086380 | A1* | 3/2019 | Harding ................. G01N 21/94 |

FOREIGN PATENT DOCUMENTS

KR  20020031831  5/2002

* cited by examiner

Primary Examiner — Samuel P Siefke
(74) Attorney, Agent, or Firm — IPLA P.A.

(57) ABSTRACT

An all-in-one self test kit includes: a test tool having a reagent container adapted to store a diagnosis reagent therein and a diagnosis kit with a casing constituted of a first body and a second body and a diagnosis strip disposed inside the casing and having a sucking part for sucking the diagnosis reagent and a diagnosis part reacting to the diagnosis reagent sucked to the sucking part; a sub-body having a container insertion portion for inserting the reagent container thereinto and a kit insertion portion for inserting the diagnosis kit thereinto; a main body for inserting the sub-body thereinto; and a cap fastened and unfastened with an entrance of the main body to open and close the main body.

9 Claims, 7 Drawing Sheets

ALL-IN-ONE SELF TEST KIT

BACKGROUND

The present invention relates to an all-in-one self test kit, and more specifically, to an all-in-one self test kit that is capable of integrating a plurality of test components with one another so that when it is tested whether a user is infected with a variety of diseases through specimens acquired from the nasal and oral cavities or from the secretion of an animal, the all-in-one self test kit can perform a diagnosis test for the infectious diseases in a simple, rapid, and convenient manner.

Respiratory diseases caused by viral respiratory infection are diseases having the highest incidence rate to thus occupy almost half of all infectious diseases. Representative respiratory viruses include adenoviruses, parainfluenza viruses (PIVs), respiratory syncytial viruses (RSVs), rhinoviruses, coronaviruses, and the like.

Under the necessity for diagnosis tests for respiratory infection and various diseases, accordingly, a variety of pre-diagnosis tests have been conducted, and among them, a molecular diagnosis generally used for the diagnosis test for the infectious disease is one of in vitro diagnostics that detects nucleic acids (DNA, RNA, or modified organisms thereof) such as bacteria, viruses, and the like to check causes of the infectious diseases and whether an infection exists or not, thereby making it possible to perform an accurate diagnosis. However, the molecular diagnosis is generally used in a laboratory where large-scale test equipment is provided, and accordingly, the diagnosis test undesirably takes a long time.

To solve such a problem, a self test kit with which a user can perform a diagnosis test simply by himself or herself has been developed, but the conventional self test kit has a large number of components, should be careful in use processes thereof, and is complicated in structure.

Patent Document: KR10-0356187B1 (Dated Oct. 18, 2002)

SUMMARY OF THE INVENTION

Accordingly, the present invention has been made to solve the above-mentioned problems, and it is an object of the present invention to provide an all-in-one self test kit that is capable of being miniaturized in size and integrating a plurality of test components with one another to perform a diagnosis for various infectious diseases in a simple, rapid, and convenient manner.

Technical Solution

To accomplish the above-mentioned objects, according to an aspect of the present invention, there is provided an all-in-one self test kit including: a test tool having a reagent container adapted to store a diagnosis reagent therein and a diagnosis kit with a casing constituted of a first body and a second body and a diagnosis strip disposed inside the casing and having a sucking part for sucking the diagnosis reagent and a diagnosis part reacting to the diagnosis reagent sucked to the sucking part; a sub-body having a container insertion portion for inserting the reagent container thereinto and a kit insertion portion for inserting the diagnosis kit thereinto; a main body for inserting the sub-body thereinto; and a cap fastened and unfastened with an entrance of the main body to open and close the main body, wherein the reagent container has a straight tube-shaped storage portion and a plurality of protrusions protruding from the inner peripheral surface of the storage portion.

According to the present invention, further, the reagent container may further include an enlarged portion extending from one end periphery of the storage portion and a sealing cover attached to an entrance of the enlarged portion to prevent the diagnosis reagent stored therein from leaking to the outside.

According to the present invention, further, the diagnosis kit may have an introduction hole formed on one side thereof to introduce the diagnosis reagent into the diagnosis strip and a sealing sheet for sealing the introduction hole.

According to the present invention, further, the main body may have an accommodation portion formed therein to insert the sub-body thereinto and a fixing part disposed on one side thereof to prevent the rotation thereof.

According to the present invention, further, the cap may have a spacing portion protruding radially from the bottom thereof, and through the spacing portion, the sub-body is limited in movements so that a space is formed between the sub-body and the cap.

To accomplish the above-mentioned objects, according to another aspect of the present invention, there is provided an all-in-one self test kit including: a test tool having a reagent container adapted to store a diagnosis reagent therein and a diagnosis kit with a casing constituted of a first body and a second body and a diagnosis strip disposed inside the casing and having a sucking part for sucking the diagnosis reagent and a diagnosis part reacting to the diagnosis reagent sucked to the sucking part; a sub-body having a container insertion portion for inserting the reagent container thereinto and a kit insertion portion for inserting the diagnosis kit thereinto; a main body for inserting the sub-body thereinto; and a cap fastened and unfastened with an entrance of the main body to open and close the main body, wherein the sub-body has a plurality of swab disposal portions for accommodating specimen collection swabs after used to treat the specimen collection swabs as waste.

Advantageous Effects

According to the present invention, the all-in-one self test kit display device is configured to allow the sub-body for insertedly keeping the test tool having the reagent container and the diagnosis kit as required to diagnose various infectious diseases to be disposed inside the main body, so that the diagnosis for the various infectious diseases can be performed in a simple, rapid, and convenient manner.

Further, the all-in-one self test kit display device according to the present invention is configured to allow the protrusions of the storage portion to come into contact with the swab during the use thereof to allow the specimen collected to the swab to be easily separated from the swab, gently flow to the diagnosis reagent, and mixed with the diagnosis reagent, thereby facilitating the reaction of the specimen to the diagnosis reagent.

Additionally, the all-in-one self test kit display device according to the present invention is configured to allow the sub-body to have the plurality of swab disposal portions for accommodating the specimen collection swabs after used therein to thus treat the specimen collection swabs as waste, so that the specimen collection swabs on which viruses may be stained can be effectively and safely thrown away.

DETAILED DESCRIPTION OF THE INVENTION

Hereinafter, embodiments of the present invention will be described with reference to the accompanying drawings.

Figure 1:
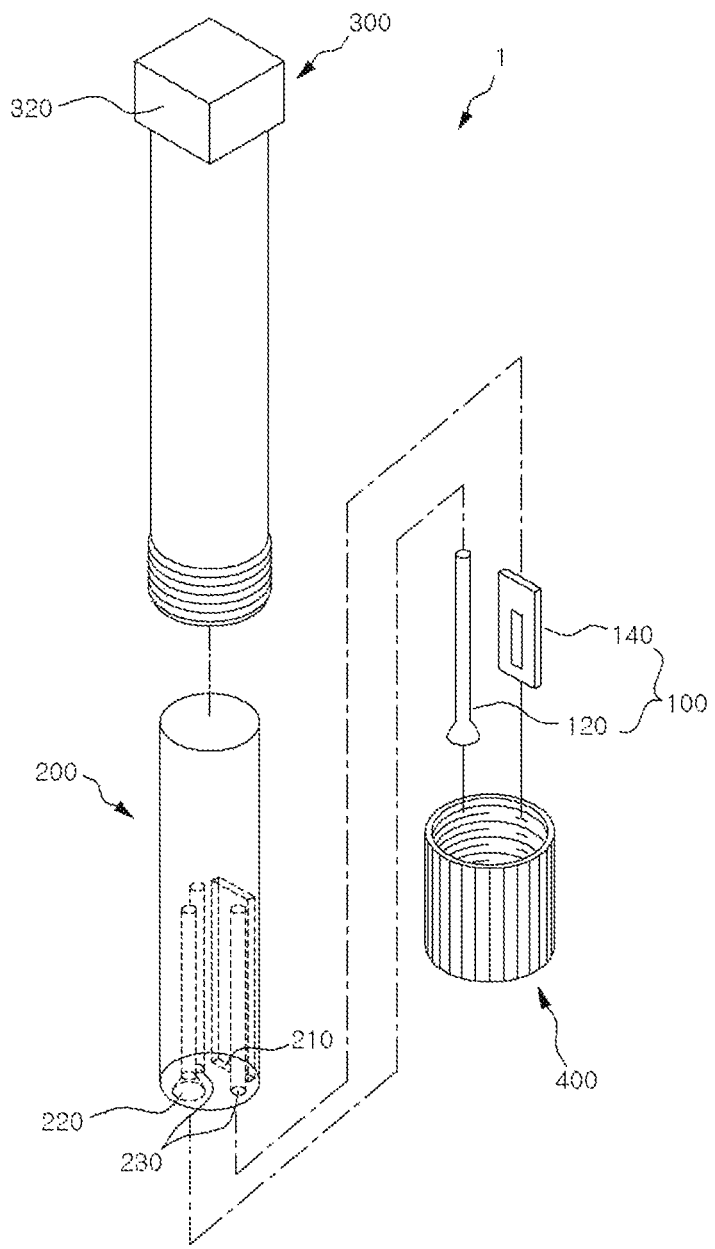
FIG. 1 is an exploded perspective view showing an all-in-one self test kit according to the present invention.
Figure 2:
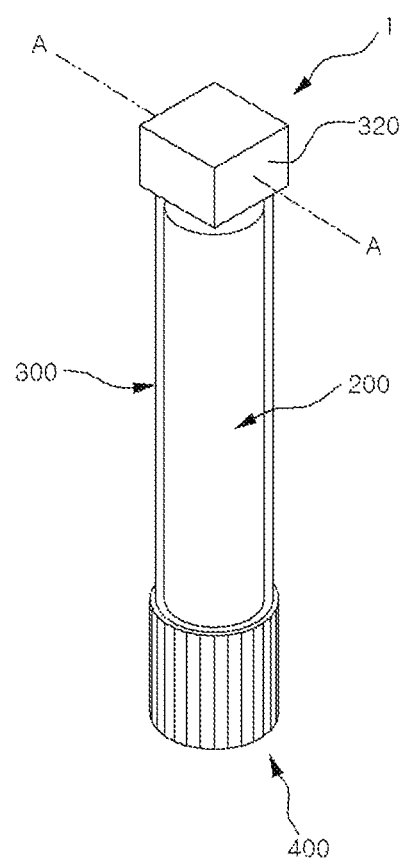
FIG. 2 is a perspective view showing the all-in-one self test kit according to the present invention.

Referring to FIGS. 1 and 2, an all-in-one self test kit 1 according to the present invention includes a test tool 100, a sub-body 200, a main body 300, and a cap 400.

Now, explanations of the respective components of the all-in-one self test kit according to the present invention will be given.

The test tool 100 is adapted to perform a diagnosis test for various infectious diseases with a user's specimen and includes a reagent container 120 and a diagnosis kit 140.

Figure 3:
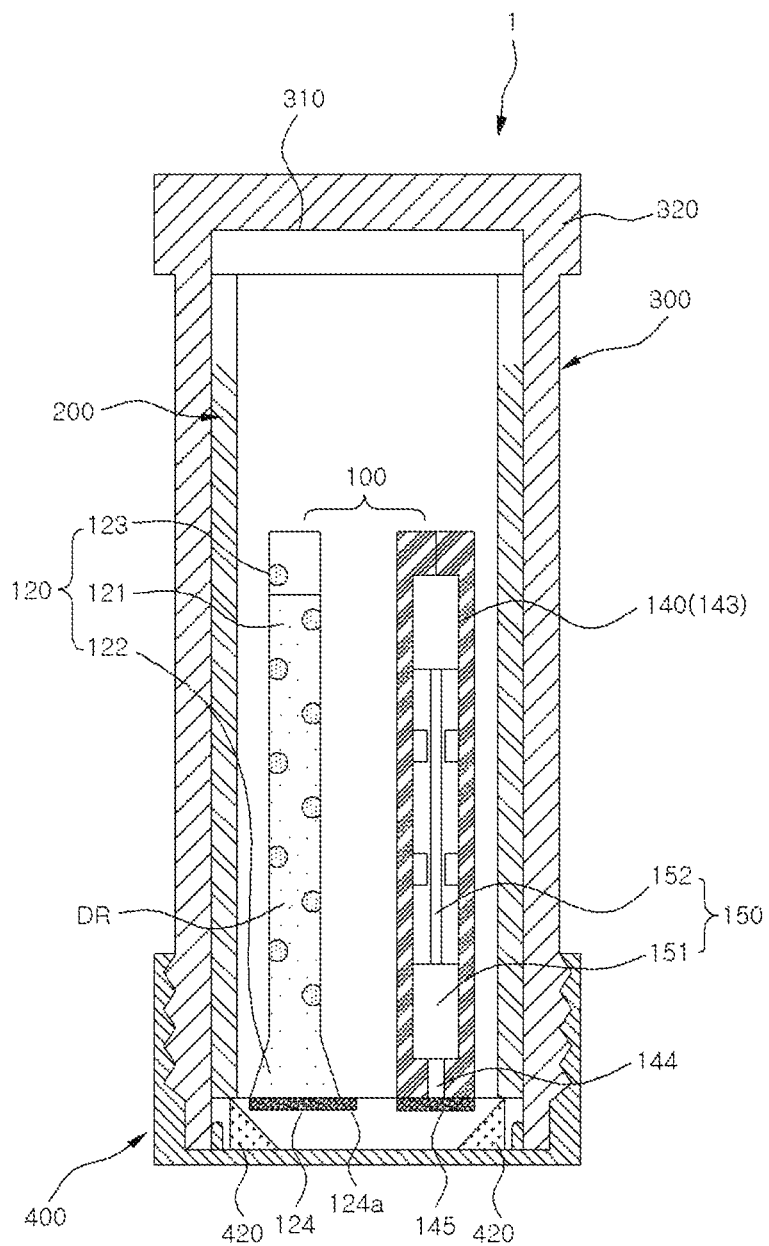
FIG. 3 is a sectional view taken along the line A-A of FIG. 2.

In specific, as shown in FIG. 3, the reagent container 120 stores a diagnosis reagent DR and includes a straight tube-shaped storage portion 121 and a frustoconically enlarged portion 122 extending from one end periphery of the storage portion 121.

Further, the storage portion 121 has a plurality of protrusions 123 protruding from the inner peripheral surface thereof in a zigzag manner.

Additionally, the enlarged portion 122 has a sealing cover 124 attached to an entrance thereof to prevent the diagnosis reagent DR stored in the reagent container 120 from leaking to the outside.

Further, the sealing cover 124 has a flap 124a disposed on one side thereof so that it can be easily separated from the entrance of the enlarged portion 122.

Figure 4:
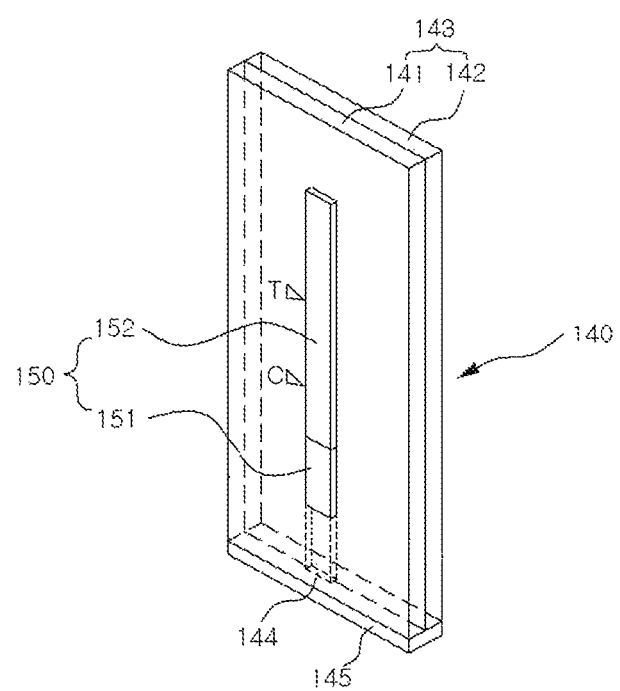
FIG. 4 is a perspective view showing a diagnosis kit of the all-in-one self test kit according to the present invention.
Figure 5:
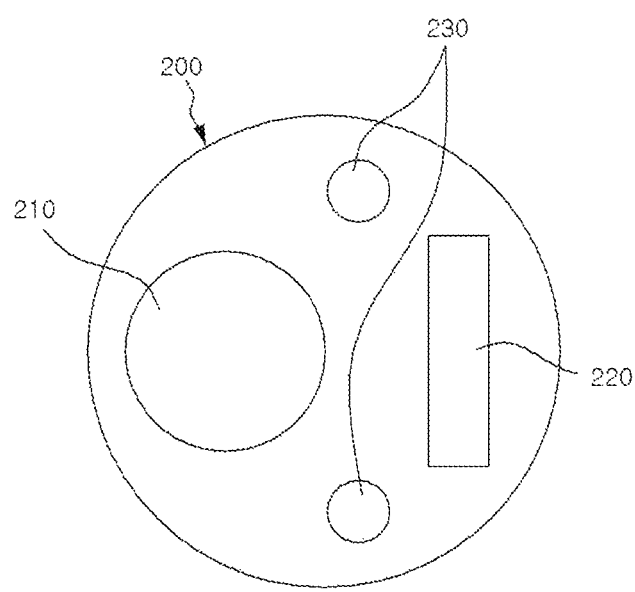
FIG. 5 is a plan view showing a sub-body of the all-in-one self test kit according to the present invention.

As shown in FIG. 4, the diagnosis kit 140 includes a casing 143 constituted of a first body 141 and a second body 142 and a diagnosis strip 150 disposed inside the casing 143.

In this case, the diagnosis kit 140 is inserted into a kit insertion portion 220 of the sub-body 200 as will be discussed later so that it can be prevented from being contaminated by contamination sources, but so as to more reliably prevent the occurrence of the contamination by the contamination sources, even the diagnosis strip 150 of the diagnosis kit 140 is sealed with the kit insertion portion 220 of the sub-body 200.

Further, the diagnosis kit 140 has an introduction hole 144 formed on one side thereof to introduce the diagnosis reagent DR into the diagnosis strip 150 and a sealing sheet 145 for sealing the introduction hole 144.

Moreover, the diagnosis kit 140 is made of a transparent material so that a diagnosis result as the reaction of the diagnosis strip 150 to the diagnosis reagent DR introduced through the introduction hole 144 can be checked with the naked eye.

The diagnosis strip 150 includes a sucking part 151 for sucking the diagnosis reagent DR and a diagnosis part 152 reacting to the diagnosis reagent DR sucked to the sucking part 151, thereby determining whether the user is infected with an infectious disease.

According to the present invention, the diagnosis part 152 of the diagnosis strip 150 is made of a material such as nitrocellulose, and as a reaction result (for example, color development) occurring by the coupling reaction with the diagnosis reagent DR is observed, it can be detected whether the user is infected with the infectious disease.

The sub-body 200 is adapted to accommodate the specimen container 120 and the diagnosis kit 140 therein and includes a container insertion portion 210 for inserting the specimen container 120 and the kit insertion portion 220 for inserting the diagnosis kit 140.

Further, the sub-body 200 has a plurality of swab disposal portions 230 for accommodating specimen collection swabs S after used to thus treat the specimen collection swabs S as waste, so that the specimen collection swabs S on which viruses may be stained can be effectively and safely thrown away.

Moreover, the sub-body 200 is made of a transparent material so that in the state where the diagnosis kit 140 is inserted into the kit insertion portion 220, the diagnosis result of the diagnosis strip 150 can be checked with the naked eye.

According to another embodiment of the present invention, the diagnosis reagent DR, not the reagent container 120 may be stored directly in the container insertion portion 210, while considering that the shape of the container insertion portion 210 corresponds to that of the reagent container 120.

In this case, the sealing cover 124 is directly attached to the end surface of the sub-body 200.

The main body 300 has an accommodation portion 310 adapted to insert the sub-body 200 thereinto and is made of a transparent material so that the diagnosis result of the diagnosis strip 150 can be checked with the naked eye.

Further, the main body 300 is cylindrical and has a fixing part 320 disposed on one side thereof.

The fixing part 320 is polygonal so that it can prevent the cylindrical main body 300 from moving when the main body 300 lies down.

Figure 6:
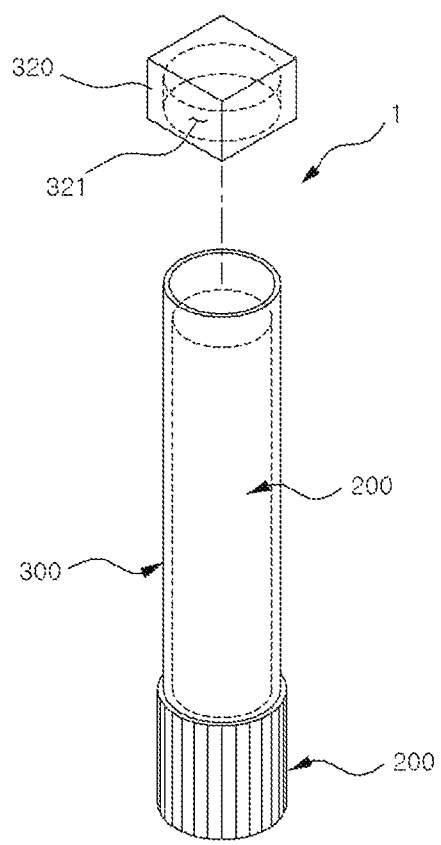
FIG. 6 is a perspective view showing a state where a fixing part is coupled to a main body in the all-in-one self test kit according to the present invention.

Further, as shown in FIG. 1, the fixing part 320 may be formed unitarily with one side of the main body 300, and otherwise, as shown in FIG. 6, the fixing part 320 may be made separately from the main body 300, while having a seating groove 321 formed therein to be coupled to one side of the main body 300.

However, the fixing part 320 is not limited to the above-mentioned structures, and only if the fixing part 320 is configured to prevent the main body 300 from moving, it can be freely shaped.

The cap 400 is fastened or unfastened with an entrance of the main body 300 to open or close the main body 300.

The cap 400 has a spiral structure formed on the inner peripheral surface thereof to correspond to a spiral structure formed on the entrance of the main body 300, so that the cap 400 is separably fastened to the man body 300, and further, the cap 400 has a spacing portion 420 formed on the bottom thereof.

The spacing portion 420 protrudes from the bottom of the cap 400 radially, and through the spacing portion 420, the sub-body 200 is limited in movements, so that a space is formed between the sub-body 200 and the cap 400.

Further, the spacing portion 420 serves as a space in which the diagnosis reagent DR discharged from the reagent container 120 is stored in a process of using the all-in-one self test kit 1 according to the present invention, and accordingly, the diagnosis reagent DR is introduced into the diagnosis kit 140 through the introduction hole 144.

Figure 7:
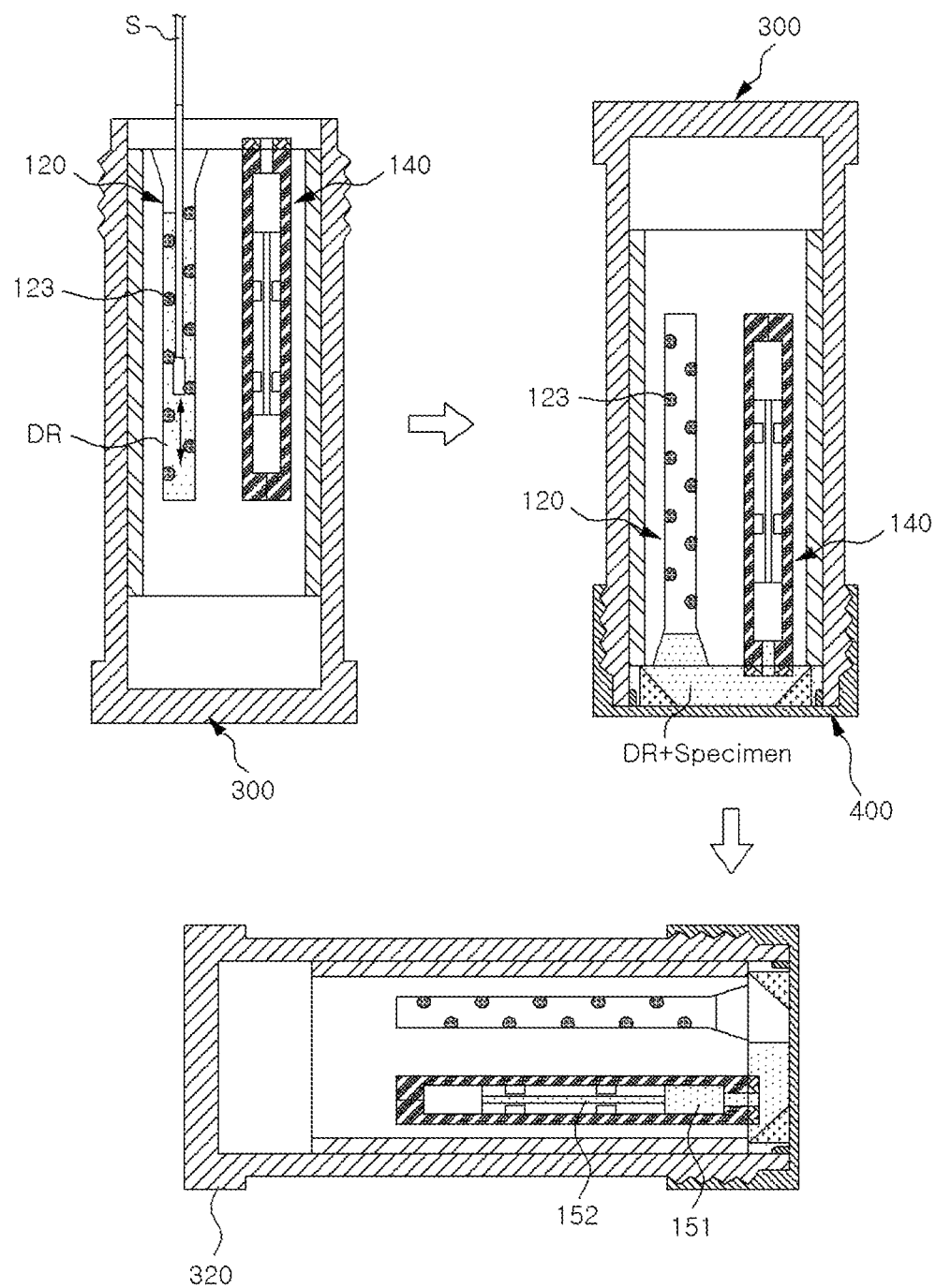
FIG. 7 is a sectional view showing a use state of the all-in-one self test kit according to the present invention.

Referring to FIG. 7, a use state of the all-in-one self test kit 1 according to the present invention will be explained below.

First, the main body 300 is open through the cap 400. Next, the sealing cover 124 is removed from the entrance of the enlarged portion 122.

After that, specimens are collected from the oral and nasal cavities of a test subject through the swabs S, and each swab S is submergedly located for a given period of time in the storage portion 121 of the reagent container 120 in which the diagnosis reagent DR is stored. Next, the swab S moves up and down in the storage portion 121 for a given period of time.

In this case, the protrusions 123 of the storage portion 121 come into contact with the swab S to allow the specimen collected to the swab S to be easily separated from the swab S, gently flow to the diagnosis reagent DR, and mixed with the diagnosis reagent DR, thereby facilitating the reaction of the specimen to the diagnosis reagent DR.

The sealing sheet 145 for the introduction hole 144 of the diagnosis kit 140 is punched to open by means of a handle portion of the used swab S, and next, the used swab S is inserted into the swab disposal portion 230 and thrown away.

After that, the cap 400 is closed to seal the entrance of the main body 300, and the main body 300 stands up so that the cap 400 is disposed on the floor.

In this case, a given space is formed between the main body 300 and the cap 400 through the spacing portion 420 of the cap 400, and a mixture of the specimen and the diagnosis reagent DR, which is stored in the storage portion 121, moves to the inside of the cap 400.

Simultaneously, the mixture of the specimen and the diagnosis reagent DR moves to the diagnosis strip 150 through the introduction hole 144 of the diagnosis kit 140.

The mixture of the specimen and the diagnosis reagent DR moves to the diagnosis part 152 through the sucking part 151, and after the mixture stands by for a given period of time, the main body 300 lies down horizontally. Next, the mixture stands by for a given period of time again.

In this case, the fixing part 320 serves to fix the main body 300 in position to prevent the diagnosis reagent DR from moving inside the main body 300, so that the reaction of the diagnosis strip 150 to the diagnosis reagent DR can be induced gently.

Accordingly, reliability in the diagnosis result of the diagnosis strip 150 can be enhanced.

Further, the all-in-one self test kit 1 according to the present invention can be used for a human body, but without being limited thereto, of course, the all-in-one self test kit 1 may be used to check the infection of livestock, birds, fish and shellfish, and the like.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. An all-in-one self test kit comprising:
   a main body, wherein the main body has a main body interior, where the main body interior comprises a sub-body, wherein the sub-body has a sub-body interior, wherein the sub-body interior comprises:
   a reagent container, wherein the reagent container has a straight tube-shaped storage portion and a plurality of protrusions protruding from an inner peripheral surface of the storage portion, wherein the reagent container has a diagnosis reagent stored therein; and
   a diagnosis container, wherein the diagnosis container has a casing, wherein the casing includes a first body and a second body, wherein diagnosis container has a diagnosis strip disposed inside the casing and a sucking part for sucking the diagnosis reagent and a diagnosis part reacting to the diagnosis reagent sucked to the sucking part; and
   a cap, wherein cap removably engages the main body to open and close an entrance to the main body interior.

2. The all-in-one self test kit according to claim 1, wherein the storage portion includes opposite first and second peripheral ends, wherein the second peripheral end is closed, wherein the first peripheral end faces the cap, wherein the reagent container further comprises an enlarged portion located at the first peripheral end and a sealing cover attached to an entrance of the enlarged portion to prevent the diagnosis reagent stored therein from leaking to the outside.

3. The all-in-one self test kit according to claim 2, wherein the enlarged portion tapers inwardly going in the direction from the enlarge portion to the second peripheral end to define a frustoconical shape.

4. The all-in-one self test kit according to claim 1, wherein the diagnosis container has an introduction hole formed on one side thereof to introduce the diagnosis reagent into the diagnosis strip and a sealing sheet for sealing the introduction hole.

5. The all-in-one self test kit according to claim 1, wherein the main body has a fixing part disposed on one side thereof to prevent the rotation thereof.

6. The all-in-one self test kit according to claim 1, wherein the cap has a spacing portion protruding radially from the bottom thereof, wherein the spacing portion contacts the sub-body to limit movement of the sub-body and form a space between the sub-body and the cap when the cap engages the main body to close the entrance to the main body interior.

7. The all-in-one self test kit according to claim 1, wherein the reagent container is located outside the diagnosis container, wherein the reagent container and the diagnosis container are arranged in a side-by-side relationship.

8. The all-in-one self test kit according to claim 1, wherein the sub-body has a plurality of swab disposal recesses, wherein the recesses are located outside of the testing container and the reagent container, wherein the swab disposal recesses are configured to accommodating specimen collection swabs after use to treat the specimen collection swabs as waste.

9. The all-in-one self test kit according to claim 1, wherein the cap has a spacing portion protruding radially from the bottom thereof, wherein the spacing portion contacts the sub-body to limit movement of the sub-body and form a space between the sub-body and the cap when the cap engages the main body to close the entrance to the main body interior, wherein the storage portion includes opposite first and second peripheral ends, wherein the second peripheral end is closed, wherein the first peripheral end faces the cap, wherein the reagent container further comprises an enlarged portion located at the first peripheral end and a sealing cover attached to an entrance of the enlarged portion to prevent the diagnosis reagent stored therein from leaking to the outside.

* * * * *